(12) United States Patent
Rimer et al.

(10) Patent No.: US 10,285,961 B2
(45) Date of Patent: *May 14, 2019

(54) ORGANIC ACIDS AS AGENTS TO DISSOLVE CALCIUM MINERALS IN PATHOLOGICAL CALCIFICATION AND USES THEREOF

(71) Applicants: Jeffrey D. Rimer, Houston, TX (US); Jihae Chung, Houston, TX (US); John Asplin, Chicago, IL (US)

(72) Inventors: Jeffrey D. Rimer, Houston, TX (US); Jihae Chung, Houston, TX (US); John Asplin, Chicago, IL (US)

(73) Assignee: University of Houston System, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,863

(22) Filed: Apr. 27, 2015

(65) Prior Publication Data

US 2015/0297545 A1  Oct. 22, 2015

Related U.S. Application Data

(63) Continuation-in-part of application No. 14/616,035, filed on Feb. 6, 2015.

(60) Provisional application No. 61/936,542, filed on Feb. 6, 2014.

(51) Int. Cl.
| A61K 31/194 | (2006.01) |
| A61K 45/06 | (2006.01) |
| C07C 59/245 | (2006.01) |

(52) U.S. Cl.
CPC .......... A61K 31/194 (2013.01); A61K 45/06 (2013.01); C07C 59/245 (2013.01)

(58) Field of Classification Search
CPC ..... A61K 31/194; A61K 45/06; C07C 59/245
See application file for complete search history.

(56) References Cited

U.S. PATENT DOCUMENTS

| 4,888,182 | A | 12/1989 | Pak |
| 5,783,603 | A | 7/1998 | Majeed et al. |
| 6,770,782 | B1 | 8/2004 | Majeed et al. |
| 7,063,861 | B2 | 6/2006 | Majeed et al. |
| 2002/0115694 | A1 | 8/2002 | Voziyan et al. |
| 2003/0207942 | A1* | 11/2003 | Bhaskaran ........... A61K 31/194 514/574 |
| 2008/0268075 | A1* | 10/2008 | Samuel ................ A61K 36/185 424/729 |
| 2015/0099704 | A1 | 4/2015 | Rimer et al. |

FOREIGN PATENT DOCUMENTS

| EP | 0429157 B1 | 3/1995 | |
| GB | 2091998 | * 8/1982 | ............. A61K 31/19 |
| WO | WO-0105250 A1 | 1/2001 | |
| WO | WO-2005087218 A1 | 9/2005 | |
| WO | WO-2007011740 A2 | 1/2007 | |

OTHER PUBLICATIONS

Chung ("Inhibition of Calcium Oxalate Monohydrate Crystallization Using Organic Growth Modifiers", Univ. Houston Thesis, May 2013).*
Rowe et al. ("Handbook of Pharmaceutical Excipients", 6th Ed, 2009, pp. 355-356, 640-642, 864 provided).*
Soygur, T. et al, Effect of Potassium Citrate Therapy on Stone Recurrence and Residual Fragments After Shockwave Lithotripsy in Lower Caliceal Calcium Oxalate Urolithiasis: A Randomized Controlled Trial, Journal of Endourology, 2002, vol. 16, No. 3, pp. 149-152.
Pak, C.Y.C. et al, Successful Management of Uric Acid Nephrolithiasis with Potassium Citrate, Kidney International, 1986, vol. 30, No. 3, pp. 422-428.
Vladimir Badmaev, Rediscovery of Hydroxycitric Acid a Versatile Nutraceutical, www.garcitrin.com/media/hca-garcitrin.pdf. available online on or before Oct. 25, 2013.
Hida et al 2005, Production of hydroxycitric acid by microorganisms, Biosci. Biotechnol. Biochem, 69 (8): 1555-1561.
Jena et al 2002, Chemistry and Biochemistry of (−)-Hydroxycitric Acid from Garcinia, Journal of Agricultural and Food Chemistry 50(1):10-22.

* cited by examiner

*Primary Examiner* — Robert H Havlin
(74) *Attorney, Agent, or Firm* — Winstead PC

(57) ABSTRACT

In an embodiment of the present disclosure, there is provided a composition for dissolving calcium oxalate crystals thereby inhibiting/preventing further growth of crystals. In some embodiments, such a composition comprises at least one stereoisomer of hydroxycitrate, a derivative of the organic acid citrate. Such a method comprises administering to the subject an effective amount of the aforementioned composition. In another embodiment, the present disclosure pertains to a method of treating kidney stone disorder. Such a method comprises administering to a subject in need thereof a therapeutically effective amount of the aforementioned composition. In yet another embodiment, the present disclosure relates to a method of treating calcium oxalate stone disease. In an embodiment, the method comprises administering to a subject in need thereof a therapeutically effective amount of the aforementioned composition.

10 Claims, 12 Drawing Sheets

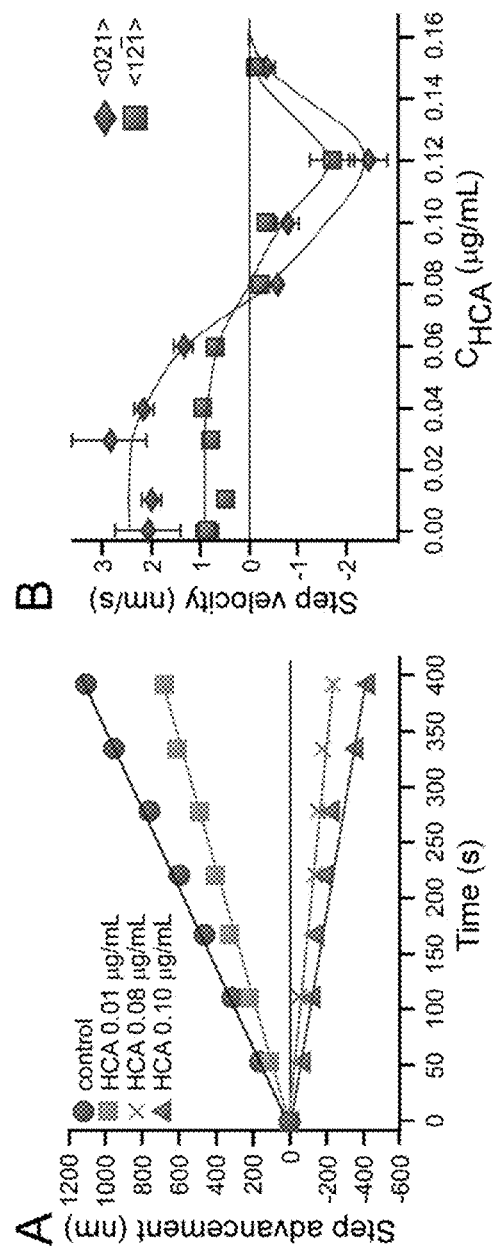

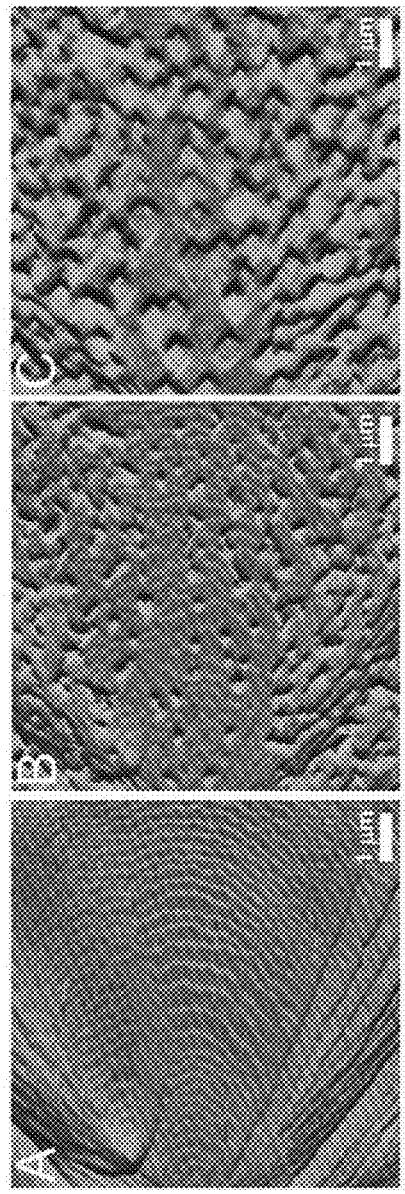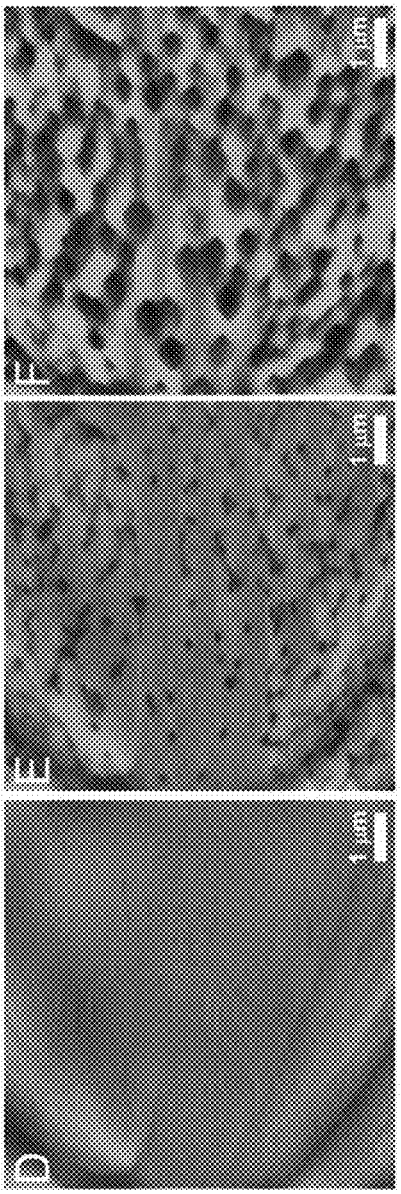

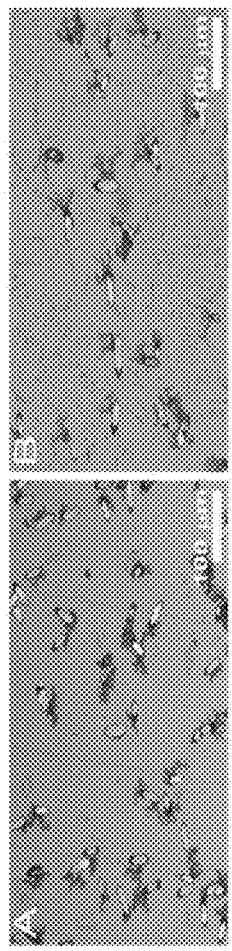
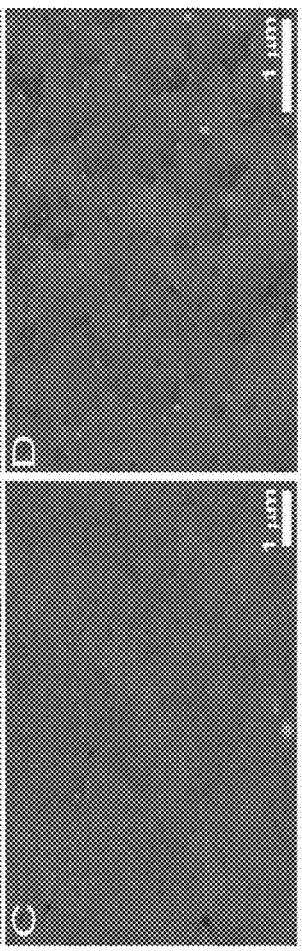
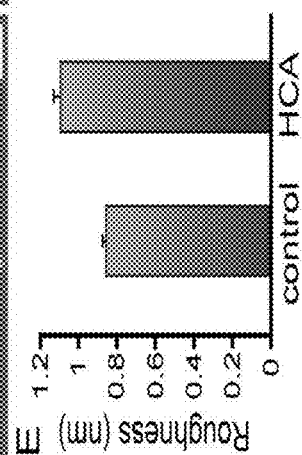
Fig. 5A
Fig. 5B
Fig. 5C
Fig. 5D
Fig. 5E

ORGANIC ACIDS AS AGENTS TO DISSOLVE CALCIUM MINERALS IN PATHOLOGICAL CALCIFICATION AND USES THEREOF

CROSS-REFERENCE TO RELATED APPLICATIONS

This application is a continuation-in-part of U.S. patent application Ser. No. 14/616,035, filed on Feb. 6, 2015, which claims priority to U.S. Provisional Application No. 61/936,542 filed on Feb. 6, 2014. The entireties of the aforementioned applications are incorporated herein by reference.

STATEMENT REGARDING FEDERALLY SPONSORED RESEARCH

This invention was made with government support under Grant No. 1207441, awarded by the National Science Foundation. The government has certain rights in the invention.

BACKGROUND

Calcium oxalate is the most common constituent of urinary calculi and relatively large crystals of this salt are frequently found in freshly voided urine from patients with recurrent calcium-containing stones. Current treatments of calcium oxalate monohydrate (COM) stone disease include water intake, diet supervision, and alkalization agents, which collectively reduce calcium oxalate super saturation in urine. Hydrochlorothiazide, sodium potassium phosphate, potassium citrate, and allopurinol are drugs available for the treatment of calcium oxalate stone disease and reported to reduce its recurrence. While these treatments can be effective, they do not completely prevent stone recurrence. In addition, many of the current treatments have significant adverse effects. Therefore, there is a need to develop more effective drugs for preventing calcium oxalate stone formation with fewer side effects.

BRIEF SUMMARY

In some embodiments, the present disclosure provides a composition for dissolving calcium oxalate crystals. In some embodiments, the calcium oxalate crystal comprises calcium oxalate monohydrate (COM). In some embodiments, the calcium oxalate crystals comprise a renal stone. In an embodiment, such a composition comprises at least one stereoisomer of hydroxycitrate (HCA), a derivative of the organic acid citrate. In some embodiments, the stereoisomers are selected from the group consisting of (2S,3R) HCA, (2R,3S) HCA, (2S,3S) HCA, (2R,3R) HCA, or combinations thereof. In an embodiment the composition comprises (2S,3R) HCA. In another embodiment the composition comprises (2R,3S) HCA. In another embodiment the composition comprises (2S,3S) HCA. In another embodiment the composition comprises (2R,3R) HCA. In an embodiment, the composition further comprises a pharmaceutically acceptable carrier. In a preferred embodiment, the composition is in a form suitable for oral administration.

In another embodiment, the present disclosure provides a composition for dissolving calcium phosphate (CaP) crystals. In some embodiments of the present disclosure, the calcium phosphate crystals comprise a renal stone. In some embodiments of the present disclosure, such a composition comprises at least one stereoisomer of hydroxycitrate (HCA), a derivative of the organic acid citrate. In some embodiments, the stereoisomers are selected from the group consisting of (2S,3R) HCA, (2R,3S) HCA, (2S,3S) HCA, (2R,3R) HCA, or combinations thereof. In an embodiment the composition comprises (2S,3R) HCA. In another embodiment the composition comprises (2R,3S) HCA. In another embodiment the composition comprises (2S,3S) HCA. In another embodiment the composition comprises (2R,3R) HCA. In an embodiment, the composition further comprises a pharmaceutically acceptable carrier. In a preferred embodiment, the composition is in a form suitable for oral administration.

In another embodiment of the present disclosure, there is provided a method of controlling calcium oxalate crystal growth in a subject in need thereof. In some embodiments, the calcium oxalate crystal comprises calcium oxalate monohydrate (COM). In an embodiment, the method comprising administering to the subject an effective amount of the aforementioned composition. In some embodiments, the subject has kidney stone disorder. In another embodiment, the subject has renal calcification disorder. In yet another embodiment, the subject has biomineralization induced disease. In a related embodiment, the method comprises administering the aforementioned composition post lithotripsy. In an embodiment, the administration of the aforementioned composition post lithotripsy prevents growth of any remaining crystal fragments.

In some embodiments the present disclosure pertains to a method of controlling calcium phosphate crystal growth in a subject in need thereof. In some embodiments, such a method comprises administering to the subject an effective amount of the aforementioned composition.

In some embodiment of the present disclosure, there is provided a method of treating kidney stone disorder. Such a method comprises administering to a subject in need thereof a therapeutically effective amount of the aforementioned composition. In some embodiments, the composition is effective in dissolving the kidney stone thereby treating the kidney stone disorder. In some embodiment, the kidney stone comprises of calcium oxalate. In some embodiments, the kidney stone comprises of calcium phosphate.

In an embodiment, the present disclosure relates to a method of treating calcium oxalate stone disease. In some embodiment, such a method comprises administering to a subject in need thereof a therapeutically effective amount of the aforementioned composition.

As set forth in more detail herein, the methods and compositions of the present disclosure provide numerous improvements in treating, preventing, or dissolving calcium oxalate and calcium phosphate crystal growth and related stone diseases.

BRIEF DESCRIPTION OF THE FIGURES

FIGS. 2A-2F shows time-elapsed images obtained via in situ atomic force microscopy (AFM). Top images represent deflection mode (FIG. 2A-FIG. 2C) and bottom images are corresponding height images (FIG. 2D-FIG. 2F) of a growth hillock on the (010) face of COM crystals in the absence (FIG. 2A, FIG. 2D) and in the presence of 0.1 μg/mL HCA (FIG. 2B-FIG. 2C, FIG. 2E-FIG. 2F). In the absence of HCA, the rectangular hillocks on the (010) face are bounded by {12-1} and {021} steps where the screw dislocation propagates in both the [12-1] and [021] directions. In the presence of 0.1 μg/mL HCA, the crystal surfaces reveal signs of dissolution. The step advancement in both the

Figures 2A, 2B, 2C, 2D, 2E, 2F:
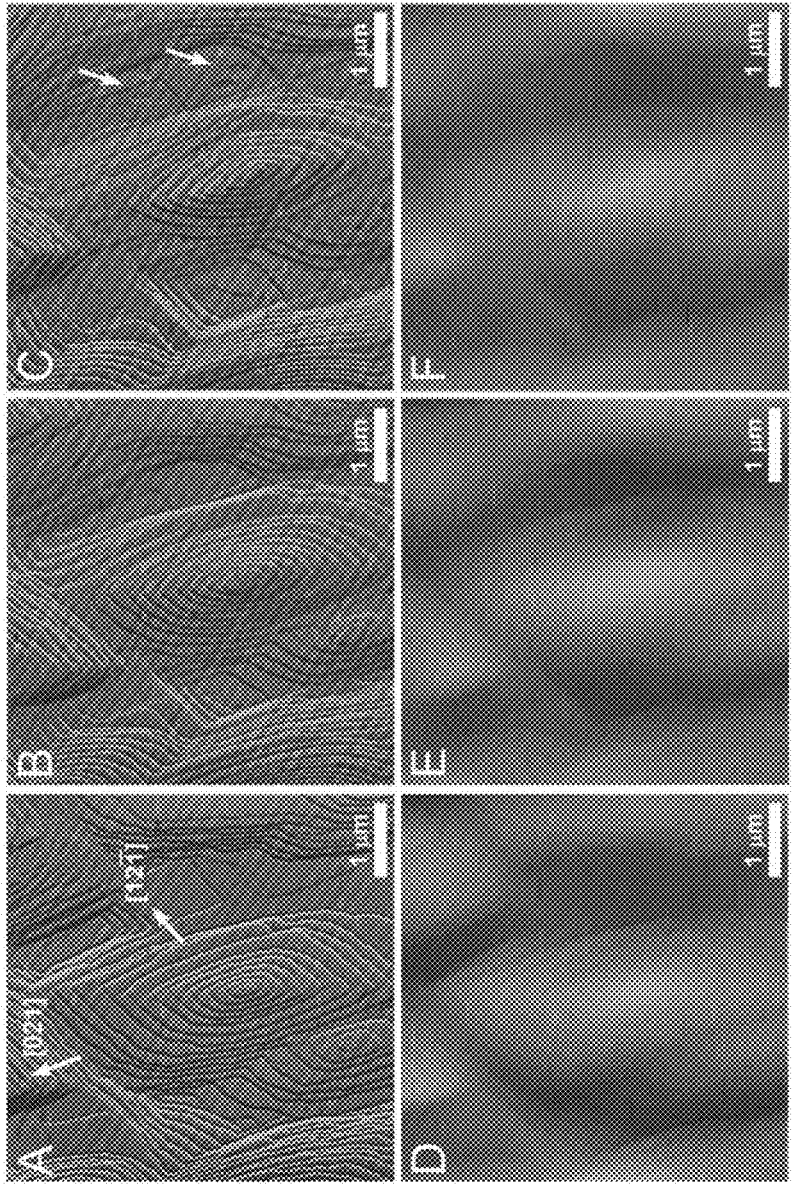
Figure 6:
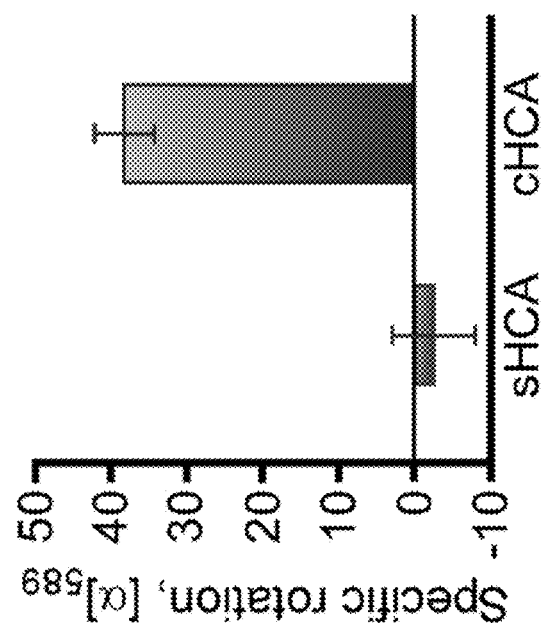
Figure 7:
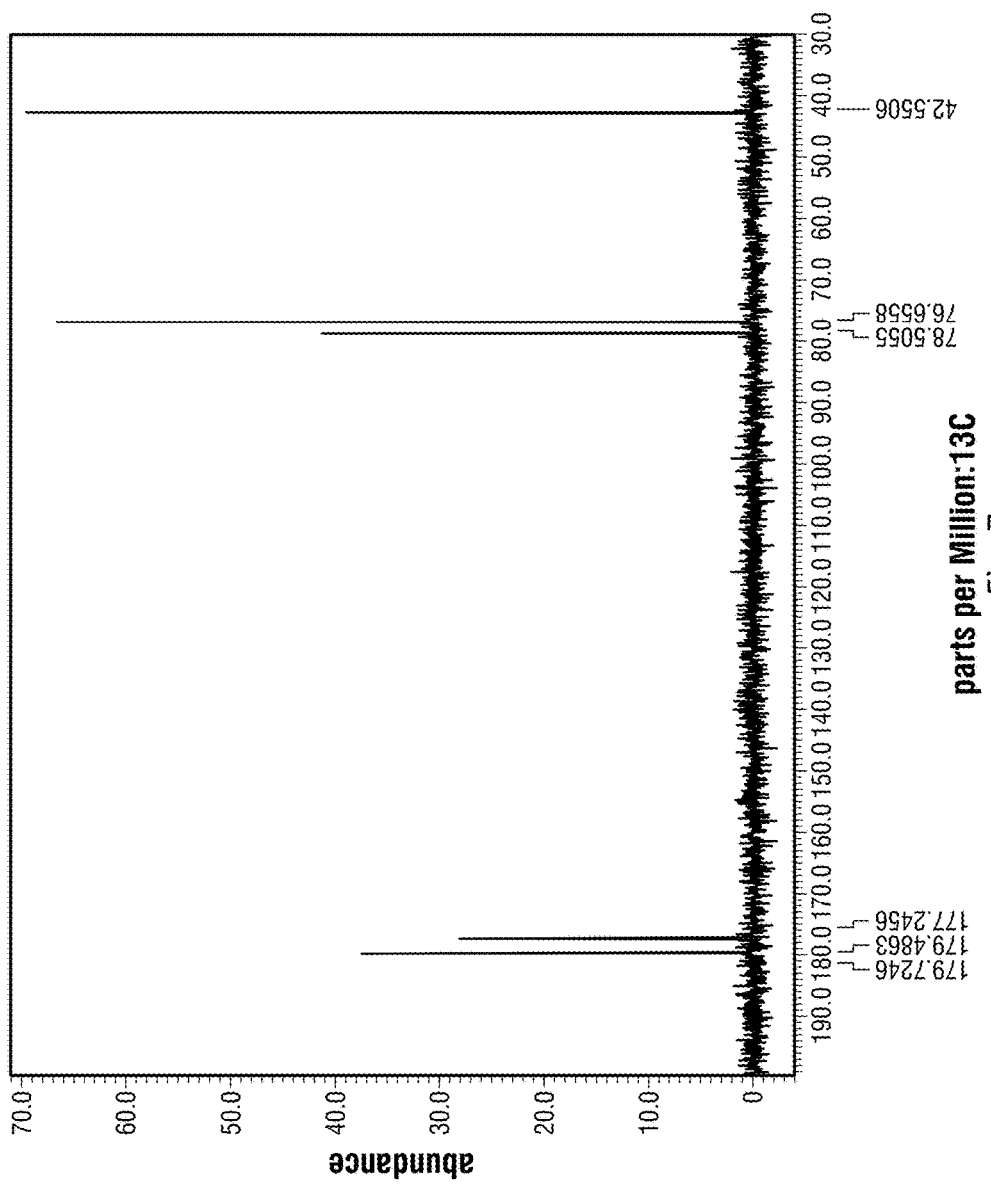
Figure 8:
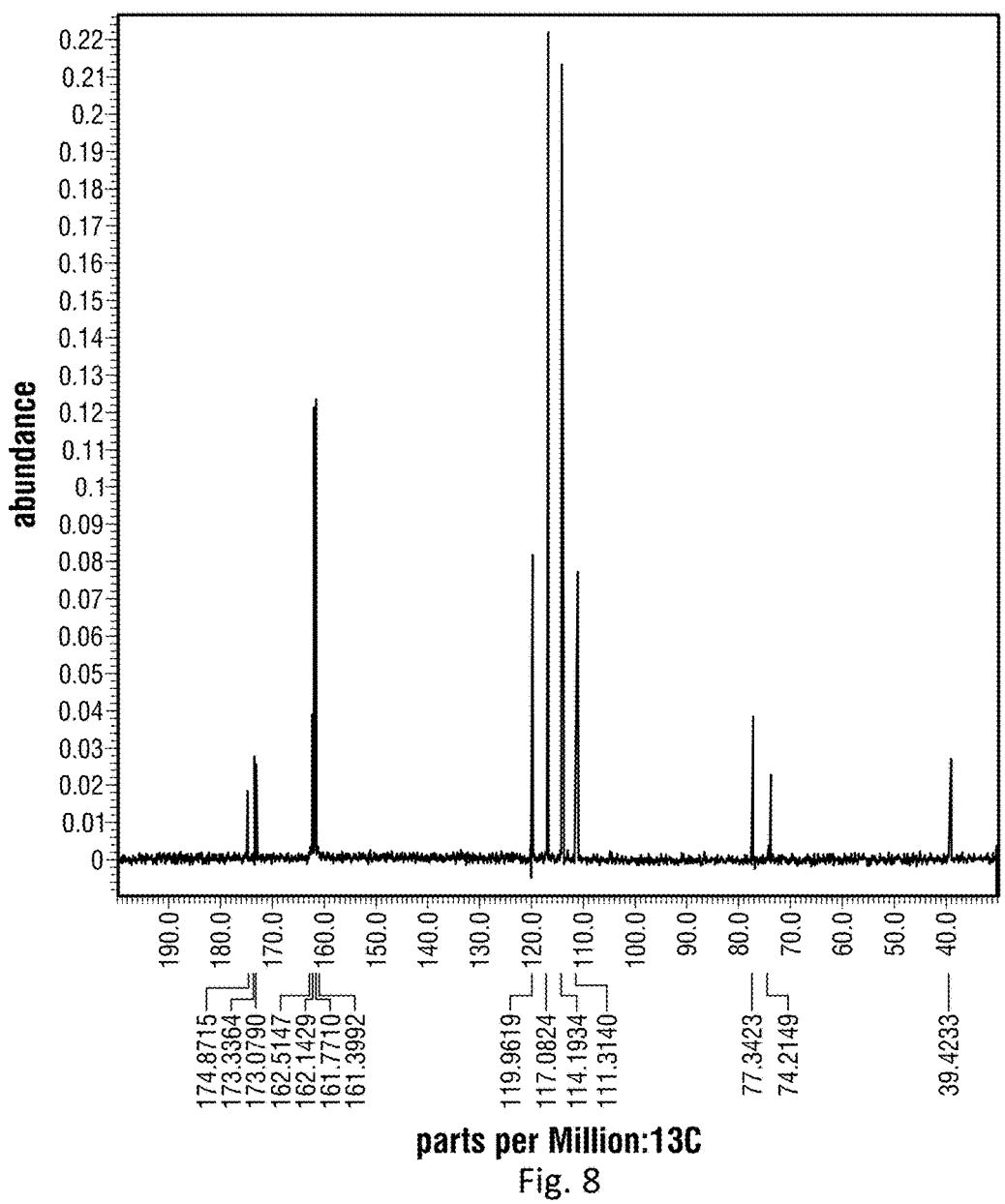

[12-1] and [021] directions reverse their direction and recede towards the center of the screw dislocation. In addition, etch pits start to form on crystal surfaces as indicated by the white arrows in C;

FIGS. 3A-3B shows plots of step advancement of the growth hillocks on the (010) crystal surface in FIG. 2. The step velocity was measured in (FIG. 3A) from successive AFM images taken over time in both <021> and <12-1> directions in the absence and in the presence of HCA at wide range of growth inhibitor concentration (B). In the presence of low concentration of HCA (<0.06 µg/mL), the step velocity in both directions decrease, whereas at high concentration of HCA (>0.15 µg/mL), the step velocity is nearly zero (i.e., fully arrested growth). However, at intermediate concentrations (0.06 µg/mL<$C_{HCA}$<0.15 µg/mL) the steps reveal negative velocity, i.e., the steps recede towards the screw dislocation center, which indicates dissolution and is a rare occurrence that to our knowledge is not reported in the literature;

FIGS. 4A-4F shows time-elapsed images obtained via in situ atomic force microscopy. Top images represent deflection mode (FIG. 4A-FIG. 4C) and bottom images are corresponding height images (FIG. 4D-FIG. 4F) of a growth hillock on the (100) face of COM crystals in the absence (FIG. 4A, FIG. 4D) and in the presence of 0.1 µg/mL HCA (FIG. 4B-FIG. 4C, FIG. 4E-FIG. 4F). The triangular hillocks on the (100) face are bounded by {12-1} steps that propagate along the c-direction. In the presence of 0.25 µg/mL HCA, etch pits start to form at step edges on the (100) face of COM crystals, which indicates dissolution of the crystal surface;

FIGS. 5A-5E shows optical micrographs (FIG. 5A, FIG. 5B) and AFM height images of surface topology (FIG. 5C, FIG. 5D) in the absence and in the presence of HCA. COM crystals in the absence of HCA (i.e., control) exhibit hexagonal platelets (FIG. 5A). The overall crystal morphology remained the same as that of the control when HCA (100 µg/mL) was introduced to the COM crystals at the end of crystallization period (3 days). However, a closer examination of the crystal surface via AFM revealed roughened crystal surface when the crystals were in contact with HCA most likely due to surface dissolution. Crystal surface roughness measured via the AFM instrument software (FIG. 5E) reveals ca. 30% increase in root-mean-square surface roughness;

FIG. 6 compares the optical rotation values for synthetic hydroxycitrate obtained from Sigma Aldrich (labelled sHCA) and extracted hydroxycitrate from *garcinia cambogia* obtained from ChromaDex (labelled cHCA);

FIG. 7 shows $C^{13}$ NMR spectrum of synthetic hydroxycitrate (sHCA);

FIG. 8 shows $C^{13}$ NMR spectrum of extracted hydroxycitrate (cHCA).

Figure 9:
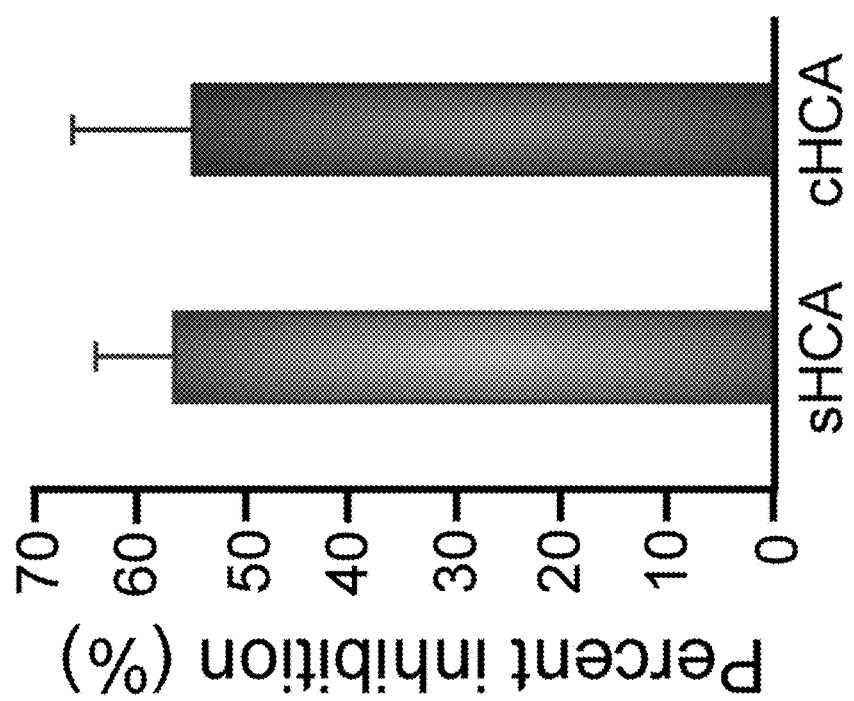
Figure 10:
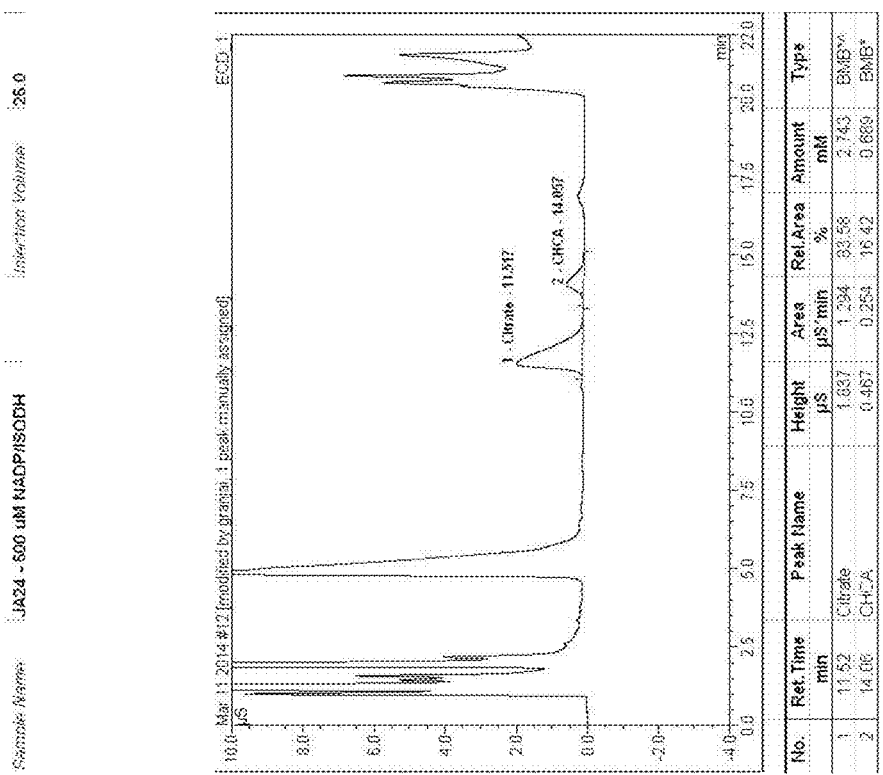
Figure 11:
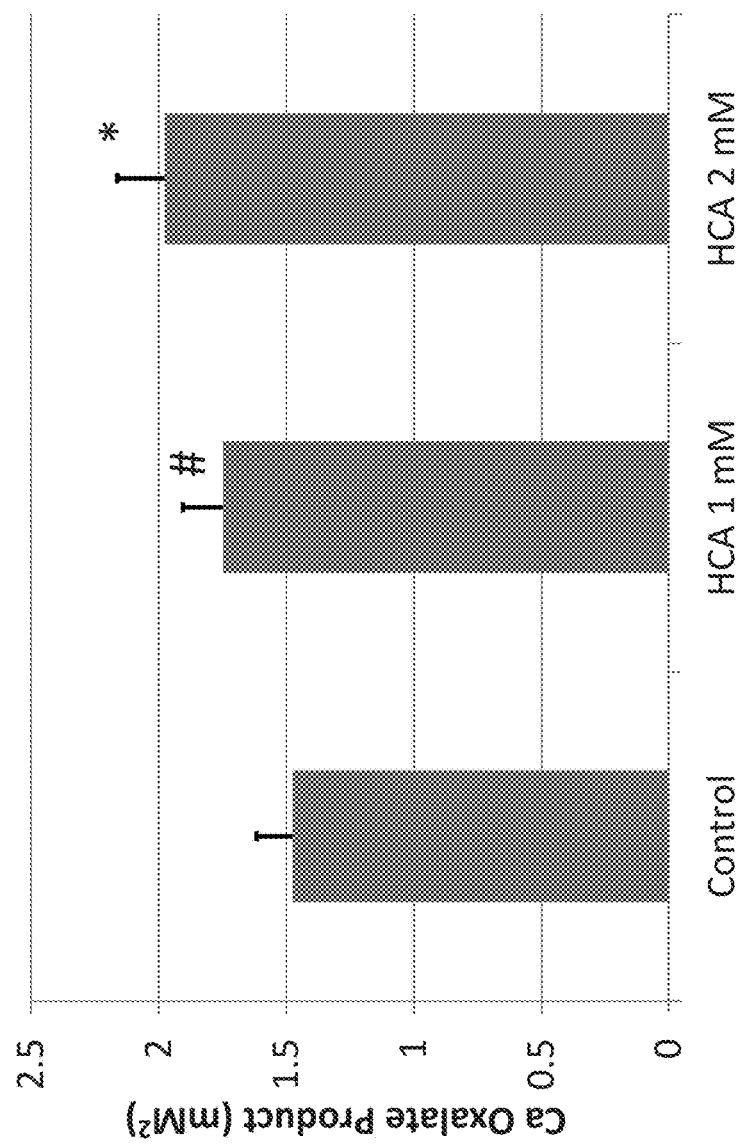
Figure 12:
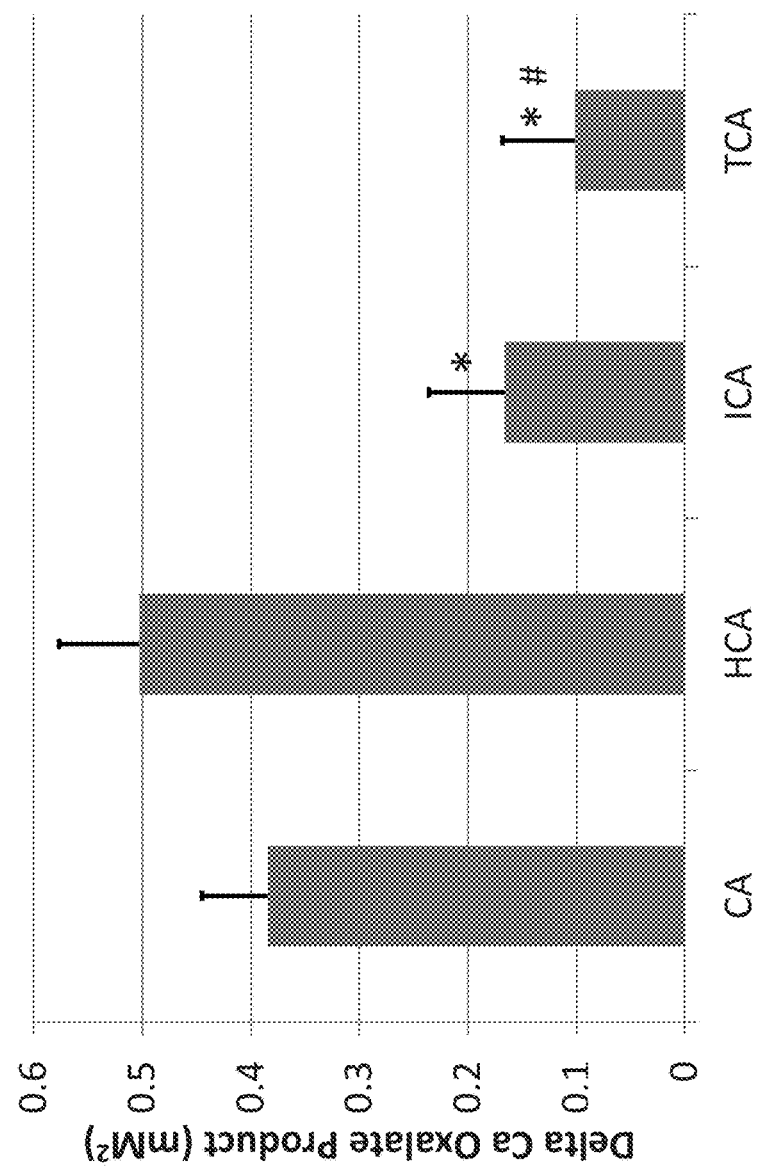

FIG. 9 shows the comparable effect of synthetic hydroxycitrate (sHCA) and extracted hydroxycitrate (cHCA) on COM crystallization;

FIG. 10 shows renal excretion of hydroxycitrate after oral ingestion;

FIG. 11 shows the effect of hydroxycitrate on the upper limit of metastability of urine from patients with kidney stones; and FIG. 12 shows effects of tricarboxylic acids on the upper limit of metastability of urine from patients with kidney stones (* differs from HCA, p<0.01; # differs from CA, p<0.05).

DETAILED DESCRIPTION

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

The following definitions are provided for specific terms which are used in the following written description.

Unless defined otherwise, all technical and scientific terms used herein have the meaning commonly understood by a person skilled in the art to which the invention belongs. The following references provide one of skill with a general definition of many of the terms used in this disclosure: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ ed., R. Reigers et al. (eds.), Springer Verlag (1991); and Hale & Marham, The Harper Collins Dictionary of Biology (1991).

The term "treating" or "treatment" as used herein is meant to refer to the administration of a compound or composition according to the present invention to dissolve kidney stones or to slow the growth of stones that are already present in the kidneys or prevent formation of new kidney stones.

Reference herein to "therapeutic" and "prophylactic" is to be considered in their broadest contexts. The term "therapeutic" does not necessarily imply that a mammal is treated until total recovery. Similarly, "prophylactic" does not necessarily mean that the subject will not eventually contract a disease condition. Accordingly, therapy and prophylaxis include amelioration of the symptoms of a particular condition or preventing or otherwise reducing the risk of developing a particular condition. The term "prophylaxis" may be considered as reducing the severity of onset of a particular condition. Therapy may also reduce the severity of an existing condition or the frequency of acute attacks.

As used herein, the term "Subject" includes animals and humans requiring intervention or manipulation due to a disease state, treatment regimen or experimental design.

The present disclosure pertains to organic molecules that are effective dissolving agents of calcium oxalate crystallization, which is the most common constituent of human kidney stones (nephrolithiasis). Specifically, the present disclosure pertains to the use of hydroxycitrate, both its synthetic analogues and extracted analogues, as growth inhibitors of calcium oxalate and calcium phosphate (CaP) crystals, which is another common kidney stone constituent. Current therapies for calcium oxalate stone disease include citrate supplements. Citrate is a small organic molecule that is a moderate inhibitor of calcium oxalate crystallization and it complexes with calcium in solution. However, citrate does not dissolve calcium oxalate crystals. In contrast, the calcium oxalate crystal dissolving agents disclosed herein provide a more potent inhibition of calcium oxalate crystallization through dissolution.

Crystallization is ubiquitous in biological systems where interactions between inorganic (salt, ions, etc.) and organic components (proteins, lipids, etc.) often mediate physiological processes in the human body, such as bone and teeth formation. Under abnormal physiological conditions, mineralization can lead to such pathologies as atherosclerotic plaques or vascular calcifications, kidney stones, gallstones, gout, and osteoarthritis. Small molecules that inhibit abnormal biomineralization are potentially effective therapies against such conditions.

Kidney stone disease is a common pathological disorder. Approximately 10-15% of the U.S. population will have a kidney stone during their lifetime, with incidence rates that are on the rise. Kidney stone pathogenesis is a complex process that involves a series of steps operating either singularly or synergistically to produce polycrystalline aggregates in the kidney. Supersaturated calcium oxalate in urine facilitates crystal nucleation and growth. The growth and aggregation of calcium oxalate crystals and the cumulative retention of crystals and/or aggregates leads to the formation of a crystalline mass that is of sufficient size to have clinical significance, i.e., is a kidney stone. Inhibiting one or more of the critical pathways of calcium oxalate stone pathogenesis, including nucleation, growth, aggregation, and retention, via the addition of external agents may potentially serve as an effective therapy for this disease.

It is well established that certain urinary constituents, such as proteins, act as natural inhibitors of calcium oxalate crystallization. A common binder group of calcium oxalate crystal inhibitors (i.e. urinary proteins and their synthetic analogues) is carboxylic acid, which binds to oxalate vacancies on calcium oxalate crystal surfaces via calcium bridges. For example, in case of calcium oxalate monohydrate crystals: $_{(COM)}COO^-$ ... $Ca^{2+}$ ... $^-OOC_{(inhibitor)}$. Several mechanisms of crystal growth inhibition have been proposed. Crystal growth inhibition may occur through the adsorption of small molecules to surfaces of crystals growing by classical nucleation and spreading of layers (so called layer-by-layer growth). Inhibitors that bind to different sites on a crystal surface (i.e. kinks, ledges, and terraces) reduce step advancement normal to that surface. Inhibitors can therefore serve to retard crystal growth, with implications in therapies for biomineralization-based diseases, or alter growth rates of specific faces, with implications in crystal shape engineering for design of advanced materials.

In some embodiments the present disclosure pertains to a composition effective for dissolving calcium oxalate crystals. In an embodiment of the present disclosure, the calcium oxalate crystals comprise a renal stone. In an embodiment, such a composition comprises at least one stereoisomer of hydroxycitrate (HCA). Hydroxycitrate exists in four stereoisomers; (2S,3R), (2R,3S), (2S,3S), (2R,3R). In some embodiments of the present disclosure, the stereoisomer HCA is selected from the group consisting of (2S,3R), (2R,3S), (2S,3S), (2R,3R) or combinations thereof. In an embodiment of the present disclosure, the at least one stereoisomer is (2S,3R) HCA. In another embodiment of the present disclosure, the at least one stereoisomer is (2R,3S) HCA. In another embodiment of the present disclosure, the at least one stereoisomer is (2S,3S) HCA. In another embodiment of the present disclosure, the at least one stereoisomer is (2R,3R) HCA. In some embodiments, the molecules disclosed herein, inhibit crystal growth rates by as much as 60%. In an embodiment, the calcium oxalate crystal dissolving agent further comprises a pharmaceutically acceptable carrier.

Clinical studies of the most potent inhibitor, hydroxycitrate (HCA), reveal clearance of HCA to the kidney with oral intake. The present disclosure relates to the use of HCA and its stereoisomers as potential drugs for kidney stone disease.

In an exemplary embodiment, the compositions and methods disclosed herein may be used to treat patients suffering from recurrent stone disease. Over 75% of all renal stones comprise of calcium oxalate. For example, the compositions and methods disclosed herein may be useful to treat patients with existing stones. The compositions and methods disclosed herein may also be used to treat these patients following extracorporeal shockwave lithotripsy to help ensure passage in the urine of shattered stone particles and renal crystal deposits. The compositions and methods disclosed herein may also be effective in treating patients with primary hyperoxaluria (a genetic disease resulting in massive over-production of oxalic acid) many of whom suffer total loss of renal function in the early years of life. This could result in less frequent use of the lithotripter and other techniques now used to remove kidney stones. The compositions and the methods disclosed herein may also be used for treating patients post renal transplantation in order to prevent calcium oxalate deposition in the renal graft since many of these patients have substantial body stores of calcium oxalate following long-term dialysis. Finally, it is also contemplated that the compositions and methods disclosed herein may be used to treat patients suffering from systemic oxalosis, i.e., deposition of calcium oxalate crystals in many tissues of the body. In some embodiments, the stones being treated (or the formation of which is to be prevented) may be present in the kidney, bladder and/or urinary tract. In a further embodiment, it is also possible that other forms of treatment can be used in conjunction with administration of the compositions disclosed herein. For example, lithotripsy treatment to break up the stones can be utilized on a patient who has been treated with the compositions disclosed herein.

The compositions disclosed herein may also be used for the treatment of calcium oxalate stone disease by administering therapeutically effective amounts of the aforementioned composition to a subject in need thereof.

Accordingly, one aspect of the present disclosure that will be disclosed in more detail herein provides a composition for dissolving calcium oxalate crystals. Such a composition comprises at least one stereoisomer of hydroxycitrate (HCA). In an embodiment, the composition further comprises at least one pharmaceutically acceptable carrier. In an embodiment of the present disclosure, the at least one stereoisomer is selected from a group consisting of (2S,3R) HCA, (2R,3S) HCA, (2S,3S) HCA, (2R,3R) HCA, or combinations thereof. In an embodiment of the present disclosure, the at least one stereoisomer of hydroxycitrate is (2S,2R). In another embodiment, the at least one stereoisomer of hydroxycitrate is (2S,3R). In another embodiment of the present disclosure, the at least one stereoisomer of hydroxycitrate is (2S,3S). In yet another embodiment of the present disclosure, at least one stereoisomer of hydroxycitrate is (2R,3R). In some embodiments of the present disclosure the composition comprises stereoisomers of hydroxycitrate in various combinations. In an embodiment of the present disclosure the composition is in a form suitable for oral administration. In some embodiments of the present disclosure, the composition is effective in treating calcium oxalate stone disease. In some embodiments, the calcium oxalate stone disease is caused by calcium oxalate monohydrate. In some embodiments, the calcium oxalate stone disease comprises renal stone disease.

In an embodiment, the present disclosure also pertains to a composition for dissolving calcium phosphate crystals. In some embodiments, the composition comprises at least one stereoisomer of hydroxycitrate (HCA). In an embodiment, the composition further comprises at least one pharmaceutically acceptable carrier. In an embodiment of the present disclosure, the stereoisomers are selected from a group consisting of (2S,3R) HCA, (2R,3S) HCA, (2S,3S) HCA, (2R,3R) HCA, or combinations thereof. In some embodiments of the present disclosure, the composition is effective in treating calcium phosphate stone disease. In some embodiments, the calcium phosphate stone disease comprises renal stone disease.

In an embodiment, the present disclosure provided for a method of treating kidney stone disorder comprising administering to a subject in need thereof a therapeutically effective amount of a composition comprising at least one stereoisomer of hydroxycitrate (HCA). In an embodiment, the composition further comprises at least one pharmaceutically acceptable carrier. In an embodiment of the present disclosure, the at least one stereoisomer is selected from a group consisting of (2S,3R) HCA, (2R,3S) HCA, (2S,3S) HCA, (2R,3R) HCA, or combinations thereof. In an embodiment, the kidney stone disorder is caused by calcium oxalate crystal formation. In an embodiment, the kidney stone disorder is caused by calcium phosphate crystal formation. In an embodiment, the subject suffers from hypercalciuria, a family history of kidney stones, gout disease, hyperparathyroidism, renal tubular acidosis, hypocitraturia or hyperoxaluria. In an embodiment, the method further comprises administering the aforementioned composition to a subject in need thereof, simultaneously with a therapeutically effective amount of a calcium-based antacid. In an embodiment, the method further comprises administering the aforementioned composition to a subject in need thereof, simultaneously with a therapeutically effective amount of a diuretic or a therapeutically effective amount of alkali such as citrate. In an embodiment, the method further comprises administering the aforementioned composition to a subject in need thereof, simultaneously with a therapeutically effective amount of a carbonic anhydrase inhibitor. In an embodiment, the carbonic anhydrase inhibitor is topiramate.

In some embodiments, the present disclosure relates to a method of treating calcium oxalate stone disease comprising administering to a subject in need thereof a therapeutically effective amount of the aforementioned composition.

Applications and Advantages

Calcium oxalate is the most common type of human kidney stone, being the major component of approximately 75% of stones. The approximate number of people affected in the U.S. alone is calculated to be 10 million. In the past 30 years, there has been no major advancement in this area of research; however, there are predictions that stone disease is on the rise, and thus the discovery of new and improved drugs that inhibit calcium oxalate crystallization will be paramount. The present disclosure relates to four stereoisomers of hydroxycitrate, a citrate analogue organic acid, as a calcium oxalate crystal dissolving agent. Applicants have identified a molecule with greater efficacy than citrate, which is hydroxycitrate. In addition, Applicants have found that the synthetic form of hydroxycitrate and natural form of hydroxycitrate from fruit extract have comparable efficacy in inhibiting calcium oxalate crystallization. In situ atomic force microscopy studies reveal that hydroxycitrate may serve as a dissolving agent for calcium oxalate crystals thereby further inhibiting the growth of these crystals. Moreover, hydroxycitrate is currently available over the counter as a component of dietary supplements and therefore has an established nontoxicity. Additional benefits of hydroxycitrate is the fact that this molecule is not metabolized (or at least not to the same extent as citrate) and it does not result in substantial increases in urine pH. The latter is of interest for CaP stone formation. For instance, a drug that can also inhibit calciumoxalate and/or CaP crystal formation without increasing urine pH would be preferential for treatment of CaP stones. The present disclosure also pertains to the use of organic acids in combination as a therapy for renal stone disease.

The preferred composition depends on the method of administration, and typically comprises one or more conventional pharmaceutically acceptable carriers, adjuvants, and/or vehicles (together referred to as "excipients"). Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

Solid dosage forms for oral administration include, for example, capsules, tablets, pills, powders, and granules. In such solid dosage forms, the compounds or salts are ordinarily combined with one or more excipients. If administered, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, *acacia* gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

It will be understood by those skilled in the art that the compounds of the invention may be administered in the form of a composition or formulation comprising pharmaceutically acceptable carriers and/or excipients.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Pharmaceutically acceptable carriers are materials useful for the purpose of administering the extract, which are preferably non-toxic, i.e., safe for human intake, and may be solid, liquid or gaseous material, which are otherwise inert and medically acceptable and are compatible with the active ingredient. The pharmaceutically acceptable carrier may be a carrier of a type which has been or would be approved by the Food and Drug Administration for administration to human subjects. The pharmaceutical composition may also contain other active ingredients. For oral administration, fine powders or granules may contain diluting, dispersing and/or surface active agents, and may be presented in a draught, in water or in a syrup; in capsules in the dry state or in a non-aqueous solution or suspension, wherein suspending agents may be included; in tablets, wherein binders and lubricants may be included; or in a solution or suspension in water or other liquid or a syrup. Where desirable or necessary, flavoring, preserving, suspending, thickening or emulsifying agents may be included. Tablets and granules are preferred and these may be coated. Other excipients and modes of administration known in the pharmaceutical art also may be used.

Routes of administration include, but are not limited to oral, dermal, inhalation, injection and intravenous.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding.

Procedures for the preparation of dosage unit forms and topical preparations are readily available to those skilled in the art from texts such as Pharmaceutical Handbook. A Martindale Companion Volume Ed. Ainley Wade Nineteenth Edition The Pharmaceutical Press London, CRC Handbook of Chemistry and Physics Ed. Robert C. Weast Ph. D. CRC Press Inc.; Goodman and Gilman's; The Pharmacological basis of Therapeutics. Ninth Ed. McGraw Hill; Remington; and The Science and Practice of Pharmacy. Nineteenth Ed. Ed. Alfonso R. Gennaro Mack Publishing Co. Easton Pa.

Additional Embodiments

Reference will now be made to more specific embodiments of the present disclosure and experimental results that provide support for such embodiments. However, note that the disclosure below is for illustrative purposes and is not intended to limit the scope of the claimed subject matter in any way.

EXAMPLE 1

Materials.

Reagents used in this study were purchased from Sigma Aldrich (St. Louis, Mo.) and were used without further purification: calcium chloride dihydrate (ACS Reagent, 99+%), sodium oxalate ($Na_2C_2O_4$, >99%), and potassium hydroxycitrate tribasic monohydrate (95%). (−)-Hydroxycitric acid calcium salt (85.9%) was purchased from ChromaDex® (Irvine, Calif.) and sodium chloride (99.9% ultrapure bioreagent) was purchased from JT Baker.

EXAMPLE 2

Calcium Oxalate Monohydrate (COM) Bulk Crystallization.

Crystallization was carried out in a 20-mL glass vial by dissolving NaCl in deionized water then adding 0.7 mL of 10 mM $CaCl_2$ stock solution which was prepared in advance. The sample vial was place in an oven set to 60° C. for one hour to ensure the crystallization was performed at 60° C. Subsequently 0.7 mL of 10 mL $Na_2C_2O_4$ stock solution was added to the solution dropwise while the solution was stirred at 400 rpm. To investigate the effect of hydroxycitrate prior to COM crystallization, prepared hydroxycitrate stock solution was added to the solution dropwise at the end of three day crystallization period. A clean glass slide (ca. 1.3×1.3 $cm^2$) was placed at the bottom of the glass vial to readily collect the crystals prior to placing the vial in the oven. Final solution composition was set to be 0.7 mM $CaCl_2$: 0.7 mM $Na_2C_2O_4$: 150 mM NaCl and the amount of deionized water was adjusted to set the final volume to 10 mL. Crystallization was performed at 60° C. for three days without agitation. The glass slide was removed from the solution and dried at room temperature prior to analysis.

EXAMPLE 3

Calcium Oxalate Monohydrate (COM) Crystal Morphology Observation.

Morphology of COM crystals prepared in the absence and in the presence of OGMs were assessed and compared under optical microscope (Leica DM2500-M). Images were obtained in brightfield using reflectance.

EXAMPLE 4

Calcium Ion Selective Electrode (ISE) Measurement.

A calcium ion selective electrode (ISE, ThermoScientific with Orion 9720BNWP Ionplus® electrode) was used to measure the effect of organic growth modifiers (OGMs) on the kinetics of COM crystallization which measures the concentration of free calcium ions in solution. Samples were prepared in the similar manner as COM bulk crystallization. Final solution composition was set to be 0.5 mM $CaCl_2$: 0.5 mM $Na_2C_2O_4$: 150 mM NaCl and the measurements were performed at room temperature. During ISE measurements, the stir rate was adjusted to 1200 rpm to minimize the induction time for nucleation. OGM efficacy was measured by calculating the temporal depletion of calcium ion concentration (ppm range). The data was normalized by subtracting the concentration of the initial time point from each time point. The rate of depletion was calculated by measuring the initial slope of the crystal growth curve. The efficacy of synthetic and extracted hydroxycitrate was assessed using the percent inhibition, which was calculated by comparing the reduced slopes for each OGM relative to that of the control (i.e., absence of OGM). Prior to ISE measurements, the electrode was calibrated using a standard calcium solution (0.1 M, Orion Ion Plus), which was diluted with deionized water to three concentrations: $10^{-4}$, $10^{-3}$ and $10^{-2}$ M. The ionic strength of each solution was adjusted using a standard solution (ISA, Thermo Scientific), which was added in a 1:50 volume ratio of ISA-to-standard.

EXAMPLE 5

Atomic Force Microscopy (AFM).

Atomic force microscopy (AFM, Bruker Multimode 4) was used to study the COM crystal surface topography at a nanometer length scale. Samples were mounted on a disk covered with a thin layer of thermally curable epoxy (MasterBond EP21AOLV). The epoxy was partially cured in an oven for ca. 20 min at 60° C. prior to transferring the crystals obtained from bulk crystallization. The crystals were immobilized on the epoxy with the [100] or [010] direction oriented normal to the specimen surface by placing the sample in an oven at 60° C. for two to three hours to completely cure the epoxy. The cantilevers used in this study were silicon nitride probes with gold reflex coating and a spring constant of 0.15 N/m (Olympus, TR800PSA). AFM was also employed to observe the kinetics of crystal growth in supersaturated calcium oxalate solutions by monitoring the velocity of step advancement on the (010) surface and (100) surface of COM crystals in real time. The experiment was designed to assess the effects of a range of concentration of hydroxycitrate on step growth using a fluid cell (Bruker, MTFML) to produce an environment that mimics in situ crystallization. The fluid cell had two ports for inlet and outlet flow to maintain constant supersaturation during AFM measurements. A silicon O-ring was used to ensure no liquid leakage would occur while solutions were being continuously replenished. A dual syringe pump (CHEMYX, Fusion 200) was used to flow the solutions into the fluid cell.

EXAMPLE 6

Figure 1:
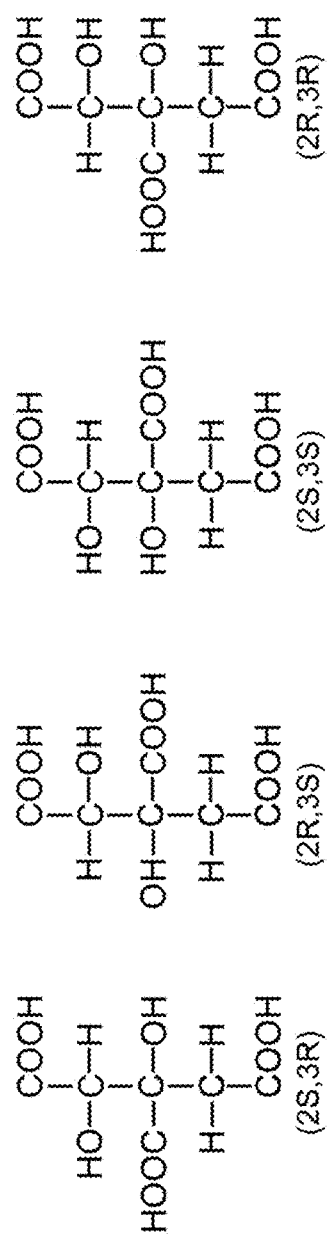
FIG. 1 shows the chemical structure of four stereoisomers of hydroxycitrate (HCA): (2S,3R) HCA, (2R,3S) HCA, (2S,3S) HCA, and (2R,3R) HCA.

Hydroxycitrate has four stereoisomers, (2S,2R), (2S,3R), (2S,3S), and (2R,3R) (FIG. 1). In order to investigate the interaction between hydroxycitrate and COM crystal surface at a molecular level, atomic force microscopy was utilized. The growth of hillocks by screw dislocation on the (010) face of COM crystals were measured in real time in the absence and in the presence of 0.1 μg/mL HCA (FIGS. 2A-2F). Growth hillocks on (010) face are bounded by {021} and {12-1} faces. The surface features of COM crystal in the presence of 0.1 μg/mL HCA suggest that HCA dissolves the COM crystal surface. The temporal advancement of steps (i.e., step velocity) of the growth hillock in the absence and in the presence of a wide range of concentration of HCA was measured (FIGS. 3A-3B). At low concentration (<0.06 μg/mL) the step velocity slightly decreases and at high concentration (>0.15 μg/mL) the step velocity ceases to zero. These phenomena are conventional modes of crystal growth inhibition. However, at intermediate concentration (0.06 μg/mL<$C_{HCA}$<0.15 μg/mL) the step velocity exhibit negative values where the steps recede back to its screw dislocation center. This phenomenon confirms the role of HCA as a dissolving agent.

EXAMPLE 7

The interaction between hydroxycitrate and the (100) surface of COM crystals was also observed using atomic force microscopy. The growth of hillocks by screw dislocation on the (100) surface of COM crystals were measured in real time in the absence and in the presence of 0.25 μg/mL HCA (FIGS. 4A-4F). Growth hillocks on the (100) surface are bounded by {12-1} faces and propagate along the c-direction. When HCA was introduced to the growth solution, its interaction with the crystal surface resulted in the rapid formation of etch pits at the edge of steps which supports the role of HCA as a dissolving agent. The surface features of COM crystals in the presence of 0.1 μg/mL HCA suggest that HCA dissolves the COM crystal surface.

EXAMPLE 8

The effect of HCA on fully grown COM crystals was studied by exposing the crystals to the dissolving agent in solution (FIGS. 5A-5F). COM crystals in the absence of HCA exhibit hexagonal platelet morphology and the COM crystals exposed to HCA maintained the same overall morphology. A closer observation of crystal surface features was conducted using atomic force microscopy and the overall surface roughness of both crystals was compared using the root-mean-square roughness value. COM crystals that were exposed to HCA revealed increased surface roughness by 30% compared to that of control COM crystals.

EXAMPLE 9

The specific rotation values (FIG. 6) and the $^{13}C$ nuclear magnetic resonance (NMR) spectra (FIGS. 7, 8) of synthetic HCA and extracted HCA reveal that they are different stereoisomers.

EXAMPLE 10

Additionally, the inhibitory efficacy of synthetic and extracted HCA was observed. An ion selective electrode measures the free calcium ion in the solution in the course of experiments. The efficacy of both HCA molecules was measured by calculating the temporal depletion of free calcium ion concentration in COM growth solutions. The data was normalized by subtracting the concentration of the initial time point from all time points. The rate of depletion was calculated by measuring the initial slope of the crystal growth curve. The efficacy of the synthetic and extracted HCA was assessed using the percent inhibition, which was calculated by comparing the slopes for each molecule relative to that of the control (i.e., in the absence of HCA). The efficacy of both hydroxycitrate molecules is comparable (FIG. 8).

EXAMPLE 9

In order for hydroxycitrate to have a direct effect on calcium oxalate stone formation, it must be excreted in the urine. As preliminary evidence of renal excretion in humans, over the counter hydroxycitrate supplements (trade name Super CitraMax) was administered to a normal healthy subject at a dose of 4.3 mmoles of hydroxycitrate two times a day (total daily dose of 8.6 mmoles) for three days. The standard dose recommended by the manufacturer is 12.9 mmoles per day. On the third day a 24 hour urine collection was performed. Hydroxycitrate excretion was measured using ion chromatography. FIG. 10 shows the chromatogram. Peak 1 is urine citrate, peak 2 is hydroxycitrate. Using a standard curve created using a high purity hydroxycitrate standard, hydroxycitrate excretion was calculated to be 1.28 mmoles per day. Thus, approximately 15% of the oral hydroxycitrate dose was excreted in the urine.

EXAMPLE 10

The crystal inhibition activity of hydroxycitrate in human urine was determined using measurement of upper limit of metastability. For this experiment, 8 urine samples from patients with kidney stones were used. The urine was either spiked with a known amount of an inhibitor or spiked with saline as control. Ten aliquots of each urine sample were added to the wells of a microtiter plate and increasing amounts of oxalate was added. The plates were incubated at 37° C. for 4 hours and then turbidity was measured using an enzyme-linked immunosorbent assay (ELISA) plate reader. The well with the lowest amount of oxalate in which increased turbidity is noted is considered the crystallization point. Multiplying the calcium concentration of the urine and the oxalate concentration (original oxalate plus the amount of oxalate added) at the point of crystallization provides a rough measure of saturation at the point of crystallization. FIG. 11 shows the results of this experiment. The y-axis is the calcium oxalate molar product at the point of crystallization and the x-axis compares urine without any inhibitor added to urine with additions of hydroxycitrate to either 1 mM or 2 mM final concentrations. The urine samples spiked with hydroxycitrate showed greater inhibition than the control urine, and there was a dose related effect with the 2 mM concentration of hydroxycitrate providing greater inhibition than the 1 mM hydroxycitrate.

EXAMPLE 11

The upper limit of metastability assay was also used to compare the inhibitory activity of hydroxycitrate to that of other tricarboxyllic acids: citrate, isocitrate, and tricarballylate. FIG. 12 shows the results of this comparison. Each of tricarboxyllic acids was added to urine samples from stone forming patients to provide a final concentration of 2 mM. The data are expressed as the increase of the calcium oxalate molar product at crystallization compared to the control urine sample without any inhibitor added. The urines spiked with hydroxycitrate showed higher levels of inhibition compared to the other inhibitors. The difference between hydroxycitrate and isocitrate or tricarballylate reached statistical significance.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of controlling calcium oxalate crystal growth in a subject in need thereof comprising:
a step of administering to the subject an effective amount of a composition consisting of:
(2S,3S) hydroxycitrate, wherein the (2S,3S) hydroxycitrate is administered at a concentration between 0.06 µg/mL and 0.15 µg/mL to dissolve a calcium oxalate crystal; and
at least one pharmaceutically acceptable carrier, wherein the at least one pharmaceutically acceptable carrier comprises at least one excipient.

2. The method of claim 1, wherein the subject has a kidney stone disorder.

3. The method of claim 1, wherein the subject has a renal calcification disorder.

4. The method of claim 1, wherein the subject has a biomineralization induced disease.

5. The method of claim 4, further comprising administering the composition post lithotripsy.

6. A method of treating kidney stone disorder in a subject comprising:
a step of administering to the subject a therapeutically effective amount of a composition consisting of:
(2S,3S) hydroxycitrate, wherein the (2S,3S) hydroxycitrate is administered at a concentration between 0.06 µg/mL and 0.15 µg/mL to dissolve a calcium oxalate crystal or calcium phosphate crystal; and
at least one pharmaceutically acceptable carrier, wherein the at least one pharmaceutically acceptable carrier comprises at least one excipient.

7. The method of claim 6, wherein the kidney stone disorder is caused by calcium oxalate crystal formation.

8. The method of claim 6, wherein the kidney stone disorder is caused by calcium phosphate crystal formation.

9. A method of treating calcium oxalate stone disease comprising:
a step of administering to a subject in need thereof a therapeutically effective amount of a composition consisting of:
(2S,3S) hydroxycitrate, wherein the (2S,3S) hydroxycitrate is administered at a concentration between 0.06 µg/mL and 0.15 µg/mL to dissolve a calcium oxalate crystal; and
at least one pharmaceutically acceptable carrier, wherein the at least one pharmaceutically acceptable carrier comprises at least one excipient.

10. A method of treating a subject with an existing kidney stone comprising:
a step of administering a therapeutically effective amount of a composition consisting of:
(2S,3S) hydroxycitrate, wherein the (2S,3S) hydroxycitrate is administered at a concentration between 0.06 µg/mL and 0.15 µg/mL to dissolve a calcium oxalate crystal or calcium phosphate crystal; and
at least one pharmaceutically acceptable carrier, wherein the at least one pharmaceutically acceptable carrier comprises at least one excipient,
wherein the administered composition leads to the dissolution of the stone.

* * * * *